(12) United States Patent
Pathak et al.

(10) Patent No.: US 7,622,135 B2
(45) Date of Patent: Nov. 24, 2009

(54) COATED STENT

(75) Inventors: Chandrashekhar Pathak, Austin, TX (US); Rama Akella, Austin, TX (US); John Ranieri, Atlanta, GA (US)

(73) Assignee: ev3 Peripheral, Inc., Plymouth, MN (US)

( * ) Notice: Subject to any disclaimer, the term of this patent is extended or adjusted under 35 U.S.C. 154(b) by 387 days.

(21) Appl. No.: 10/446,916

(22) Filed: May 27, 2003

(65) Prior Publication Data

US 2006/0165752 A1 Jul. 27, 2006

Related U.S. Application Data

(63) Continuation of application No. 09/991,235, filed on Oct. 22, 2001, now abandoned.

(51) Int. Cl.
*A61F 2/04* (2006.01)
(52) U.S. Cl. .................................. 424/426
(58) Field of Classification Search ............ None
See application file for complete search history.

(56) References Cited

U.S. PATENT DOCUMENTS

| | | | |
|---|---|---|---|
| 4,451,568 A | 5/1984 | Schneider et al. |
| 4,768,507 A | 9/1988 | Fischell et al. |
| 4,795,458 A | 1/1989 | Regan |
| 5,015,253 A | 5/1991 | MacGregor |
| 5,059,211 A | 10/1991 | Stack et al. |
| 5,135,516 A | 8/1992 | Sahtjian et al. |
| 5,140,012 A | 8/1992 | McGovern et al. |
| 5,163,952 A | 11/1992 | Froix |
| 5,240,913 A | 8/1993 | Maragnore et al. |
| 5,258,020 A | 11/1993 | Froix |
| 5,282,824 A | 2/1994 | Gianturco |
| 5,292,321 A | 3/1994 | Lee |
| 5,292,331 A | 3/1994 | Boneau |
| 5,304,121 A | 4/1994 | Sahatjian |
| 5,314,688 A | 5/1994 | Kauffman et al. |
| 5,334,201 A | 8/1994 | Cowan |
| 5,366,504 A | 11/1994 | Andersen et al. |
| 5,380,299 A | 1/1995 | Fernot et al. |
| 5,383,927 A | 1/1995 | De Goicoechea et al. |
| 5,383,928 A | 1/1995 | Scott et al. |
| 5,405,378 A | 4/1995 | Strecker |

(Continued)

FOREIGN PATENT DOCUMENTS

EP 0734 721 * 3/1996

(Continued)

OTHER PUBLICATIONS

Auer, J. et al., "Clinical Significance of Pleiotropic Effects of Statins: Lipid Reduction and Beyond," *Current Medicinal Chemistry*, vol. 9, No. 20, pp. 1831-1850 (2002).

*Primary Examiner*—Carlos A Azpuru
(74) *Attorney, Agent, or Firm*—Rissman Hendricks & Oliverio, LLP

(57) ABSTRACT

Stents with coatings comprising a combination of a restenosis inhibitor comprising an HMG-CoA reductase inhibitor and a carrier. Also provided are methods of coating stents with a combination of an HMG-CoA reductase inhibitor and a carrier. A preferred example of a restenosis inhibitor is cerivastatin. The stent coatings have been shown to release restenosis inhibitors in their active forms.

6 Claims, 5 Drawing Sheets

U.S. PATENT DOCUMENTS

| | | |
|---|---|---|
| 5,411,550 A | 5/1995 | Herweck et al. |
| 5,419,760 A | 5/1995 | Narciso, Jr. |
| 5,423,885 A | 6/1995 | Williams |
| 5,439,446 A | 8/1995 | Barry |
| 5,443,495 A | 8/1995 | Buscemi et al. |
| 5,449,382 A | 9/1995 | Dayton |
| 5,464,450 A | 11/1995 | Buscemi et al. |
| 5,464,650 A | 11/1995 | Berg et al. |
| 5,476,509 A | 12/1995 | Keogh et al. |
| 5,500,013 A | 3/1996 | Buscemi et al. |
| 5,507,771 A | 4/1996 | Gianturco |
| 5,545,208 A | 8/1996 | Wolff et al. |
| 5,545,211 A | 8/1996 | An et al. |
| 5,545,213 A | 8/1996 | Keogh et al. |
| 5,551,954 A | 9/1996 | Buscemi et al. |
| 5,554,182 A | 9/1996 | Dinh et al. |
| 5,556,413 A | 9/1996 | Lam |
| 5,571,086 A | 11/1996 | Kaplan et al. |
| 5,571,166 A | 11/1996 | Dinh et al. |
| 5,575,815 A | 11/1996 | Slepian et al. |
| 5,578,075 A | 11/1996 | Dayton |
| 5,588,352 A | 12/1996 | Harrison |
| 5,591,199 A | 1/1997 | Porter et al. |
| 5,591,227 A | 1/1997 | Dinh et al. |
| 5,593,434 A | 1/1997 | Williams |
| 5,599,352 A | 2/1997 | Dinh et al. |
| 5,603,722 A | 2/1997 | Phan et al. |
| 5,605,696 A | 2/1997 | Eury et al. |
| 5,607,467 A | 3/1997 | Froix |
| 5,609,629 A | 3/1997 | Fearnot et al. |
| 5,622,188 A | 4/1997 | Plaia et al. |
| 5,624,411 A | 4/1997 | Tuch |
| 5,628,785 A | 5/1997 | Schwartz et al. |
| 5,629,077 A | 5/1997 | Turnlund et al. |
| 5,632,771 A | 5/1997 | Boatman et al. |
| 5,632,840 A | 5/1997 | Campbell |
| 5,634,895 A | 6/1997 | Igo et al. |
| 5,637,113 A | 6/1997 | Tartaglia et al. |
| 5,649,977 A | 7/1997 | Campbell |
| 5,653,747 A | 8/1997 | Dereume |
| 5,670,161 A | 9/1997 | Healy et al. |
| 5,674,241 A | 10/1997 | Bley et al. |
| 5,674,242 A | 10/1997 | Phan et al. |
| 5,674,276 A | 10/1997 | Andersen et al. |
| 5,674,278 A | 10/1997 | Boneau |
| 5,674,287 A | 10/1997 | Slepian et al. |
| 5,697,967 A | 12/1997 | Dinh et al. |
| 5,700,286 A | 12/1997 | Tartaglia et al. |
| 5,713,949 A | 2/1998 | Jayaraman |
| 5,716,981 A | 2/1998 | Hunter et al. |
| 5,718,159 A | 2/1998 | Thompson |
| 5,718,713 A | 2/1998 | Frantzen |
| 5,725,549 A | 3/1998 | Lam |
| 5,728,751 A | 3/1998 | Patnaik |
| 5,733,327 A | 3/1998 | Igaki et al. |
| 5,766,710 A | 6/1998 | Turnlund et al. |
| 5,769,883 A | 6/1998 | Buscemi et al. |
| 5,772,629 A | 6/1998 | Kaplan |
| 5,772,668 A | 6/1998 | Summers et al. |
| 5,788,979 A | 8/1998 | Alt et al. |
| 5,797,887 A | 8/1998 | Rosen et al. |
| 5,800,538 A | 9/1998 | Slepian et al. |
| 5,804,318 A | 9/1998 | Pinchuk et al. |
| 5,824,045 A | 10/1998 | Alt |
| 5,824,049 A | 10/1998 | Ragheb et al. |
| 5,827,322 A | 10/1998 | Williams |
| 5,836,316 A | 11/1998 | Plaia et al. |
| 5,840,387 A | 11/1998 | Berlowitz-Tarrantet et al. |
| 5,843,089 A | 12/1998 | Sahatjian et al. |
| 5,843,172 A | 12/1998 | Yan |
| 5,861,027 A | 1/1999 | Trapp |
| 5,871,538 A | 2/1999 | Dereume |
| 5,873,904 A | 2/1999 | Ragheb et al. |
| 5,876,433 A | 3/1999 | Lunn |
| 5,876,449 A | 3/1999 | Starck et al. |
| 5,879,382 A | 3/1999 | Boneau |
| 5,891,108 A | 4/1999 | Leone et al. |
| 5,891,196 A | 4/1999 | Lee et al. |
| 5,893,868 A | 4/1999 | Hanson et al. |
| 5,895,407 A | 4/1999 | Jayaraman |
| 5,900,246 A | 5/1999 | Lambert |
| 5,904,146 A | 5/1999 | Plaia et al. |
| 5,928,279 A | 7/1999 | Shannon et al. |
| 5,954,744 A | 9/1999 | Phan et al. |
| 5,968,093 A | 10/1999 | Kranz |
| 5,972,027 A | 10/1999 | Johnson |
| 5,976,155 A | 11/1999 | Foreman et al. |
| 5,976,169 A | 11/1999 | Imran |
| 5,980,551 A | 11/1999 | Summers et al. |
| 6,004,943 A | 12/1999 | Shi et al. |
| 6,010,530 A | 1/2000 | Goicoechea |
| 6,015,402 A | 1/2000 | Sahota |
| 6,015,430 A | 1/2000 | Wall |
| 6,019,789 A | 2/2000 | Dinh et al. |
| 6,033,434 A | 3/2000 | Borghi |
| 6,033,436 A | 3/2000 | Steinke et al. |
| 6,036,725 A | 3/2000 | Avellanet |
| 6,039,757 A | 3/2000 | Edwards et al. |
| 6,041,305 A | 3/2000 | Sakurai |
| 6,071,305 A | 6/2000 | Brown et al. |
| 6,077,298 A | 6/2000 | Tu et al. |
| 6,080,422 A | 6/2000 | Williams |
| 6,083,257 A | 7/2000 | Taylor et al. |
| 6,086,455 A | 7/2000 | Frantzen |
| 6,086,611 A | 7/2000 | Duffy et al. |
| 6,087,552 A | 7/2000 | Gregory |
| 6,090,134 A | 7/2000 | Tu et al. |
| 6,090,135 A | 7/2000 | Plaia et al. |
| 6,096,070 A | 8/2000 | Ragheb et al. |
| 6,099,561 A | 8/2000 | Alt |
| 6,099,562 A | 8/2000 | Ding et al. |
| 6,099,563 A | 8/2000 | Zhong |
| 6,100,443 A | 8/2000 | Sims et al. |
| 6,102,943 A | 8/2000 | McGuinness |
| 6,113,628 A | 9/2000 | Borghi |
| 6,120,523 A | 9/2000 | Crocker et al. |
| 6,120,535 A | 9/2000 | McDonald et al. |
| 6,120,536 A | 9/2000 | Ding et al. |
| 6,129,757 A | 10/2000 | Weadock |
| 6,133,242 A | 10/2000 | Zalewski et al. |
| 6,146,358 A | 11/2000 | Rowe |
| 6,149,681 A | 11/2000 | Houser et al. |
| 6,159,488 A | 12/2000 | Nagler et al. |
| 6,161,399 A | 12/2000 | Jayaraman |
| 6,165,209 A | 12/2000 | Patterson et al. |
| 6,168,619 B1 | 1/2001 | Dinh et al. |
| 6,171,232 B1 | 1/2001 | Papandreou et al. |
| 6,171,609 B1 | 1/2001 | Kunz |
| 6,174,326 B1 | 1/2001 | Kitaoka et al. |
| 6,174,329 B1 | 1/2001 | Callol et al. |
| 6,177,523 B1 | 1/2001 | Reich et al. |
| 6,183,353 B1 | 2/2001 | Frantzen |
| 6,187,035 B1 | 2/2001 | Jang |
| 6,193,746 B1 | 2/2001 | Strecker |
| 6,197,047 B1 | 3/2001 | Kranz |
| 6,197,051 B1 | 3/2001 | Zhong |
| 6,206,915 B1 | 3/2001 | Fagan et al. |
| 6,206,916 B1 | 3/2001 | Furst |
| 6,210,436 B1 | 4/2001 | Weadock |
| 6,214,040 B1 | 4/2001 | Jayaraman |
| 6,214,042 B1 | 4/2001 | Jacobsen et al. |
| 6,214,115 B1 | 4/2001 | Taylor et al. |
| 6,217,607 B1 | 4/2001 | Alt |
| 6,221,099 B1 | 4/2001 | Andersen et al. |

| | | |
|---|---|---|
| 6,224,626 B1 | 5/2001 | Steinke |
| 6,231,600 B1 | 5/2001 | Zhong |
| 6,240,616 B1 | 6/2001 | Yan |
| 6,241,691 B1 | 6/2001 | Ferrera et al. |
| 6,245,104 B1 | 6/2001 | Alt |
| 6,245,760 B1 | 6/2001 | He et al. |
| 6,248,129 B1 | 6/2001 | Froix |
| 6,251,136 B1 | 6/2001 | Guruwaiya et al. |
| 6,251,142 B1 | 6/2001 | Bernacca et al. |
| 6,253,443 B1 | 7/2001 | Johnson |
| 6,254,627 B1 | 7/2001 | Freidberg |
| 6,254,632 B1 | 7/2001 | Wu et al. |
| 6,255,277 B1 | 7/2001 | Stamler et al. |
| 6,258,121 B1 | 7/2001 | Yang et al. |
| 6,263,880 B1 | 7/2001 | Parker et al. |
| 6,264,690 B1 | 7/2001 | Von Oepen |
| 6,273,908 B1 | 8/2001 | Ndondo-Lay |
| 6,273,913 B1 | 8/2001 | Wright et al. |
| 6,280,411 B1 | 8/2001 | Lennox |
| 6,290,719 B1 | 9/2001 | Garberoglio |
| 6,290,722 B1 | 9/2001 | Wang |
| 6,299,604 B1 | 10/2001 | Ragheb et al. |
| 6,306,165 B1 | 10/2001 | Patnaik et al. |
| 6,306,166 B1 | 10/2001 | Barry et al. |
| 6,315,794 B1 | 11/2001 | Richter |
| 6,325,821 B1 | 12/2001 | Gaschino et al. |
| 6,331,186 B1 | 12/2001 | Wang et al. |
| 6,331,527 B1 | 12/2001 | Parmacek et al. |
| 6,387,124 B1 | 5/2002 | Buscemi et al. |
| 6,450,989 B2 | 9/2002 | Dubrul et al. |
| 6,451,049 B2 | 9/2002 | Vallana et al. |
| 6,451,373 B1 | 9/2002 | Hossainy et al. |
| 6,468,304 B1 | 10/2002 | Dubois-Rande et al. |
| 6,475,233 B2 | 11/2002 | Trozera |
| 6,497,671 B2 | 12/2002 | Ferrera et al. |
| 6,506,437 B1 | 1/2003 | Harish et al. |
| 6,569,195 B2 | 5/2003 | Yang et al. |
| 6,585,764 B2 | 7/2003 | Wright et al. |
| 6,592,617 B2 | 7/2003 | Thompson |
| 6,596,020 B2 | 7/2003 | Vardi et al. |
| 2001/0001128 A1 | 5/2001 | Holman et al. |
| 2001/0007082 A1 | 7/2001 | Dusbabek et al. |
| 2001/0007083 A1 | 7/2001 | Roorda |
| 2001/0016770 A1 | 8/2001 | Allen et al. |
| 2001/0029351 A1 | 10/2001 | Falotico et al. |
| 2001/0032010 A1 | 10/2001 | Sandock |
| 2001/0037144 A1 | 11/2001 | Kim et al. |
| 2001/0037145 A1 | 11/2001 | Guruwaiya et al. |
| 2001/0041929 A1 | 11/2001 | Oepen |
| 2001/0044650 A1 | 11/2001 | Simso et al. |
| 2001/0044651 A1 | 11/2001 | Steinke et al. |
| 2001/0044652 A1 | 11/2001 | Moore |
| 2001/0044655 A1 | 11/2001 | Patnaik et al. |
| 2001/0047202 A1 | 11/2001 | Slaikeu et al. |
| 2001/0053928 A1 | 12/2001 | Edelman et al. |
| 2002/0002353 A1 | 1/2002 | Michal et al. |
| 2002/0002396 A1 | 1/2002 | Fulkerson |
| 2002/0002398 A1 | 1/2002 | Voinov |
| 2002/0004678 A1 | 1/2002 | Easterling |
| 2002/0004679 A1 | 1/2002 | Eury et al. |
| 2002/0004680 A1 | 1/2002 | Plaia et al. |
| 2002/0005206 A1 | 1/2002 | Falotico et al. |
| 2002/0007209 A1 | 1/2002 | Scheerder et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0044654 A1 | 4/2002 | Maeda et al. |
| 2002/0065546 A1 | 5/2002 | Machan et al. |
| 2002/0111590 A1 | 8/2002 | Davila et al. |
| 2002/0120326 A1 | 8/2002 | Michal |
| 2002/0133224 A1 | 9/2002 | Bajgar et al. |
| 2003/1000921 | 1/2003 | Yang |
| 2003/0125800 A1 | 7/2003 | Shulze et al. |

FOREIGN PATENT DOCUMENTS

| | | | |
|---|---|---|---|
| EP | 0734721 | * | 3/1996 |
| EP | 0 734 721 | A2 | 10/1996 |
| EP | 0 897 701 | A2 | 2/1999 |
| EP | 1 084 721 | A2 | 3/2001 |
| EP | 1 159 934 | A2 | 12/2001 |
| WO | WO 00/62614 | | 10/2000 |
| WO | WO 01/01890 | A1 | 1/2001 |
| WO | WO 02/47731 | A2 | 6/2002 |

* cited by examiner

COATED STENT

This application is a continuation of application Ser. No. 09/991,235, filed Oct. 22, 2001, now abandoned which application is incorporated herein by reference.

BACKGROUND

1. Field of the Invention

The present invention generally relates to stent coatings that include bioactive compounds that inhibit restenosis.

2. Description of the Related Art

Stents are often used in the treatment of atherosclerosis, a disease of the vascular system in which arteries become partially, and sometimes completely, occluded with substances that may include lipids, cholesterol, calcium, and various types of cells, such as smooth muscle cells and platelets. Atherosclerosis is a very common disease that can be fatal, and methods of preventing the accumulation of occluding compounds in arteries are being investigated.

Percutaneous transluminal angioplasty (PTA) is a commonly used procedure to break up and/or remove already formed deposits along arterial walls. PTA can also be used to treat vascular occlusions not associated with atherosclerosis. During PTA, a catheter is threaded through a patient's arteries until the occluded area to be treated is reached. A balloon attached to the end of the catheter is then inflated at the occluded site. The expanded balloon breaks up the mass of occluding substances, resulting in a more open arterial lumen. However, there is a risk that the artery may re-close within a period of from one day to approximately six months of the procedure. This re-closure is known as restenosis. Accordingly, a balloon-only angioplasty procedure often does not result in a permanently reopened artery. To prevent restenosis, scaffolding devices called stents are deployed in the lumen of the artery as a structural support to maintain the lumen in an open state. Unlike the balloon and the catheter used in an angioplasty procedure, the stent usually remains in the artery as a permanent prosthesis. Although technically feasible, removal of the stent from the artery is generally avoided.

Stents are typically elongated structures used to keep open lumens (e.g., openings in the body) found in various parts of the body so that the parts of the body containing those lumens may function properly. Stents are usually implanted at their site of use in the body by attaching them in a compressed state to a catheter that is directed through the body to the site of stent use. The stent can be expanded to a size which enables it to keep the lumen open by supporting the walls of the lumen once it is positioned at the desired site.

The lumens of blood vessels are common sites of stent deployment. Vascular stents are frequently used in blood vessels to open the vessel and provide improved blood flow. The stents are typically hollow, cylindrical structures made from struts or interconnected filaments. Vascular stents can be collapsed to reduce their diameter so that the stent can be guided through a patient's arteries or veins to reach the site of deployment. Stents are typically either coupled to the outside of the balloon for expansion by the expanding balloon or are self-expanding upon removal of a restraint such as a wire or sleeve maintaining the stent in its collapsed state.

The stent is allowed to expand at the desired site to a diameter large enough to keep the blood vessel open. Vascular stents are often made of metal to provide the strength necessary to support the occluded arterial walls. Two of the preferred metals are Nitinol alloys of nickel and titanium, and stainless steel. Other materials that can be used in fabricating stents are ceramics, polymers, and plastics. Stents may be coated with a substance, such as a biodegradable or biostable polymer, to improve the biocompatibility of the stent, making it less likely to cause an allergic or other immunological response in a patient. A coating substance may also add to the strength of the stent. Some known coating substances include organic acids, their derivatives, and synthetic polymers that are either biodegradable or biostable. Biostable coating substances do not degrade in the body, biodegradable coating substances can degrade in the body. A problem with known biodegradable and biostable stent coatings is that both types of coatings are susceptible to breaking and cracking during the temperature changes and expansion/contraction cycles experienced during stent formation and use.

Stents located within any lumen in the body may not always prevent partial or complete restenosis. In particular, stents do not always prevent the re-narrowing of an artery following PTA. In fact, the introduction and presence of the stent itself in the artery or vein can create regions of trauma such as, e.g., tears in the inner lining of the artery, called the endothelium. It is believed that such trauma can trigger migration of vascular smooth muscle cells, which are usually separated from the arterial lumen by the endothelium, into the arterial lumen, where they proliferate to create a mass of cells that may, in a matter of days or weeks, occlude the artery. Such re-occlusion, which is sometimes seen after PTA, is an example of restenosis. Coating a stent with a substance to make the surface of the stent smoother and to minimize damage to the endothelium has been one method used to create stents that are less likely to contribute to restenosis.

Currently, drug therapy for restenosis primarily consists of the systemic administration of drugs. However, delivering drugs in this manner may result in undesirable side effects in other areas of the body unrelated to the vascular occlusion. Also, the administered dose of a drug that is delivered systemically is less effective in achieving the desired effect in the local area of the body in which it is needed. For example, an anti-restenosis drug delivered systemically may be sequestered or metabolized by other parts of the body, resulting in only a small amount of the drug reaching the local area in which it is needed.

Stents with bioactive compounds or drugs in or on their coatings can be used. One class of drugs that can be used in stent coatings is restenosis inhibitors. There remains a need for coatings that can be shown to actually release the restenosis inhibiting compounds in their active forms. Further, there is a need for stents that can carry drugs and release them in a sufficient concentration to produce the desired effect. In particular, there is a need for such stents that can inhibit restenosis.

SUMMARY OF INVENTION

Broadly, the invention relates to coated stents, methods of making coated stents and methods of using coated stents. In one aspect, the invention can include a coated stent comprising a stent and a coating comprising a substantially unreacted HMG-CoA reductase inhibitor. It is preferred that the coating also comprise a carrier for the HMG-CoA reductase inhibitor. In a specific embodiment, the HMG-CoA reductase inhibitor is provided in a nonpolymeric carrier. In another embodiment, the HMG-CoA reductase inhibitor is provided in a polymeric carrier, which may be physically bound to the polymer, chemically bound to the polymer, or both. The coating composition can be a liquid solution at room and/or body temperature, which may include the HMG-CoA reductase inhibitor and the polymeric or nonpolymeric carrier, and which may additionally include a solvent which later may be removed, e.g., by drying. Alternatively, the coating composition may be a solid at room and body temperature.

The coating composition preferably includes an effective amount of the HMG-CoA reductase inhibitor. More particularly, the coating composition preferably includes an amount of the HMG-CoA reductase inhibitor that is sufficient to be therapeutically effective for inhibiting regrowth of plaque or inhibiting restenosis. In one embodiment, the coating composition may include from about 1 wt % to about 50 wt % HMG-CoA reductase inhibitor, based on the total weight of the coating composition. In another embodiment, the coating composition includes from about 5 wt % to about 30 wt % HMG-CoA reductase inhibitor. In yet another embodiment, the coating composition includes from about 10 wt % to about 20 wt % HMG-CoA reductase inhibitor. Any HMG-CoA reductase inhibitor may be used, but the HMG-CoA reductase inhibitor is preferably selected from the group consisting of cerivastatin, atorvastatin, simvastatin, fluvastatin, lovastatin, and pravastatin. More preferably, the HMG-CoA reductase inhibitor is cerivastatin. In another embodiment, the coating composition comprises more than one HMG-CoA reductase inhibitor. In another embodiment, the coating composition includes a restenosis inhibitor that is not an HMG-CoA reductase inhibitor.

In one embodiment, the coating composition comprises an effective amount of a polymeric carrier, e.g., an amount sufficient to provide a polymer matrix or support for the inhibitor. The polymer is preferably non-reactive with the HMG-CoA reductase inhibitor, i.e., no chemical reaction occurs when the two are mixed. The polymer may be a polymer having no functional groups. Alternatively, the polymer may be one having functional groups, but none that are reactive with the HMG-CoA reductase inhibitor. The polymer may include a biodegradable polymer. For example, the polymer may include a polymer selected from the group consisting of polyhydroxy acids, polyanhydrides, polyphosphazenes, polyalkylene oxalates, biodegradable polyamides, polyorthoesters, polyphosphoesters, polyorthocarbonates, and blends or copolymers thereof. The polymer may also include a biostable polymer, alone or in combination with a biodegradable polymer. For example, the polymer may include a polymer selected from the group consisting of polyurethanes, silicones, polyacrylates, polyesters, polyalkylene oxides, polyalcohols, polyolefins, polyvinyl chlorides, cellulose and its derivatives, fluorinated polymers, biostable polyamides, and blends or copolymers thereof.

In another embodiment, the coating composition comprises an effective amount of a non-polymeric carrier. In a particular embodiment, the non-polymeric carrier comprises a fatty acid. The non-polymeric carrier may alternatively comprise a biocompatible oil, wax, or gel. In a yet further embodiment, the non-polymeric carrier may comprise a mixture of one or more of a fatty acid, an oil, a wax, and/or a gel.

In another aspect, the invention can include a method of coating a stent. In a specific embodiment, the method includes providing a coating composition comprising a blend of a substantially unreacted HMG-CoA reductase inhibitor and a polymeric or nonpolymeric carrier, and applying the coating composition to the stent. Providing the coating composition may include mixing the I-IMG-CoA reductase inhibitor and a nonpolymeric liquid carrier. In one embodiment, the nonpolymeric liquid carrier comprises a C-6 to C-18 fatty acid. In another embodiment, providing the coating composition may include mixing the HMG-CoA reductase inhibitor and a polymeric liquid carrier. In a further embodiment, providing the coating composition may include mixing the HMG-CoA reductase inhibitor, a polymer, and a solvent under conditions such that the HMG-CoA reductase inhibitor does not chemically react with the polymer, or does not react to any substantial extent. Providing the coating composition may also include mixing the HMG-CoA reductase inhibitor, a polymer, and a solvent at a temperature of from about 20° C. to about 30° C., preferably at about 25° C. The method of coating the composition may further comprise removing the solvent by, e.g., drying. In another embodiment, providing a coating composition may include providing a solid coating comprising an HMG-CoA reductase inhibitor and a polymer.

In another embodiment, a method of coating a stent may further comprise expanding the stent to an expanded position before applying the coating composition to the stent. The coating composition may be applied to the stent by any number of ways, e.g., by spraying the coating composition onto the stent, by immersing the stent in the coating composition, or by painting the stent with the coating composition. Other coating methods, such as electrodeposition can also be used. In one embodiment, excess coating composition is allowed to drain from the stent. In another embodiment, the stent is dried after the coating composition is applied to the stent to provide a solid coating composition. The coating composition may be formed into a solid film that is then applied to the stent by wrapping the film around the stent.

In another aspect, the invention includes a method of treating an occluded artery comprising providing a stent, providing a coating composition comprising a nonpolymeric or polymeric carrier and a HMG-CoA reductase inhibitor in an amount effective to prevent or substantially reduce restenosis, applying the coating composition to the stent, and deploying the stent in the occluded artery at the site of occlusion. Providing a coating composition may comprise dissolving or suspending an amount of the HMG-CoA reductase inhibitor effective to prevent or substantially reduce restenosis in a nonpolymeric carrier that is a liquid at room and/or body temperature. In another embodiment, providing a coating composition may comprise dissolving in a polymeric carrier that is a liquid at room and/or body temperature an amount of the HMG-CoA reductase inhibitor effective to prevent or substantially reduce restenosis in an occluded vascular lumen. In alternative embodiments, the nonpolymeric or polymeric carrier may be a solid at room and body temperature. Where a polymeric carrier is provided, the HMG-CoA reductase inhibitor may be physically bound to the polymer, chemically bound to the polymer, or both. The coating composition may be a solution which includes the HMG-CoA reductase inhibitor, the polymer, and a solvent. The solvent may be removed by, e.g., drying the stent or other methods known in the art to yield a stent having a solid polymeric carrier for the HMC-CoA reductase inhibitor. The coating composition may include an amount of the HMG-CoA reductase inhibitor that is therapeutically effective for inhibiting regrowth of plaque or inhibiting restenosis. More particularly, the coating composition may include from about 1 wt % to about 50 wt % HMG-CoA reductase inhibitor, based on the total weight of the coating composition.

In another aspect, the invention can include a method of treating restenosis, comprising inserting a coated stent into a body lumen, the coated stent comprising a stent and a coating composition comprising a substantially unreacted HMG-CoA reductase inhibitor and a nonpolymeric or polymeric carrier, which may be a liquid at room and body temperature, a solid at room and body temperature, or a solid at room temperature and a liquid at body temperature. In one embodiment, the coated stent releases the HMG-CoA reductase inhibitor in an amount sufficient to inhibit or reduce the regrowth of plaque. In another embodiment, the coated stent releases the HMG-CoA reductase inhibitor in an amount sufficient to inhibit or reduce restenosis.

In another aspect, the invention can include a method of localized delivery of an HMG-CoA reductase inhibitor, comprising inserting a coated stent into a body lumen, the coated stent comprising a stent and a coating composition comprising a substantially unreacted HMG-CoA reductase inhibitor and a polymeric or nonpolymeric carrier. In one embodiment, the coated stent releases the HMG-CoA reductase inhibitor in an amount effective to inhibit the regrowth of plaque. In another embodiment, the coated stent releases the HMG-CoA reductase inhibitor in an amount effective to inhibit restenosis.

DETAILED DESCRIPTION OF THE PREFERRED EMBODIMENT

Figure 1:
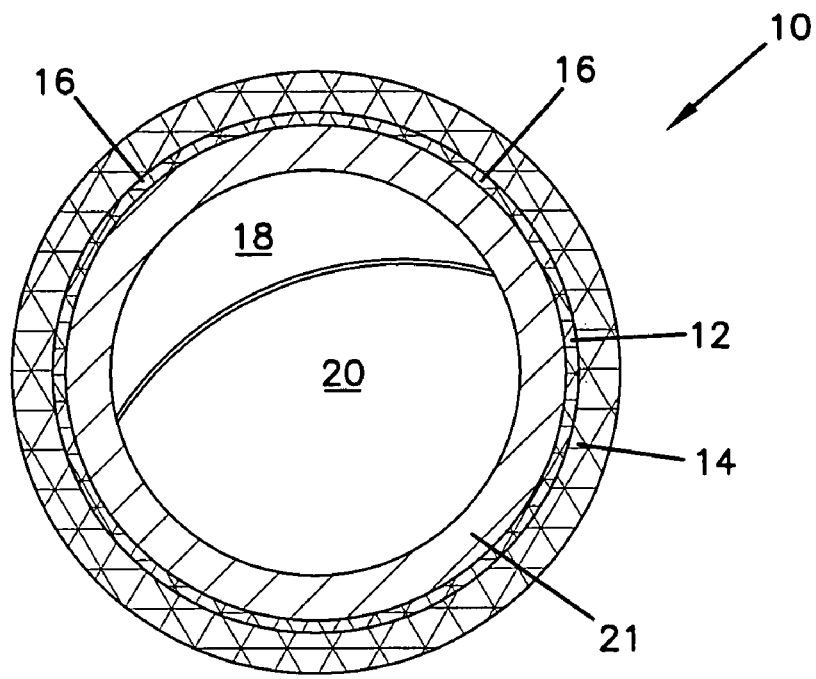
FIG. 1 is a cross-section of an artery experiencing restenosis in the presence of an uncoated stent.

An exemplary artery 10 experiencing restenosis is shown in FIG. 1. The endothelium 12 normally serves as a solid barrier between the layer of smooth muscle cells 14 and the arterial lumen 20. Small tears 16 in the endothelium 12 can expose smooth muscle cells 14, which can then migrate into the arterial lumen 20 and hyperproliferate into a mass 18 which can partially or completely occlude the lumen 20 even though an uncoated stent 21 is placed, during a procedure such as angioplasty, in the artery 10 to keep the arterial lumen 20 open.

Figure 2:
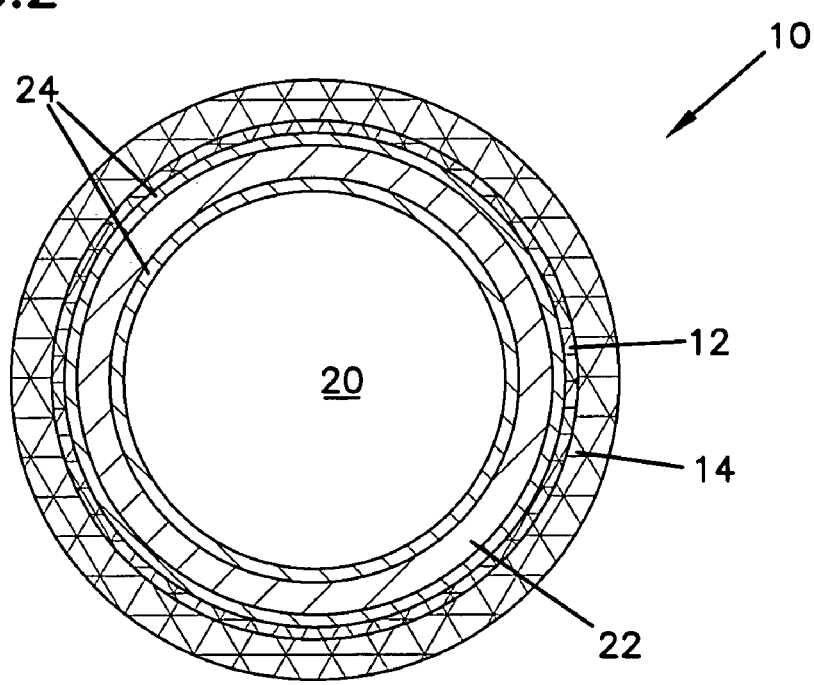
FIG. 2 is a cross-section of an artery containing a coated stent.

An artery 10 containing a coated stent 22 prepared according to an embodiment herein is shown in FIG. 2. The stent has a coating 24 containing a polymer and a bioactive compound that inhibits restenosis. By using a stent having this coating 24, the tears 16 shown in FIG. 1 in the endothelium 12 may be reduced or eliminated. Additionally, the mass 18 created by a proliferation of smooth muscle cells 14, as shown in FIG. 1, is eliminated or substantially reduced.

Figure 3:
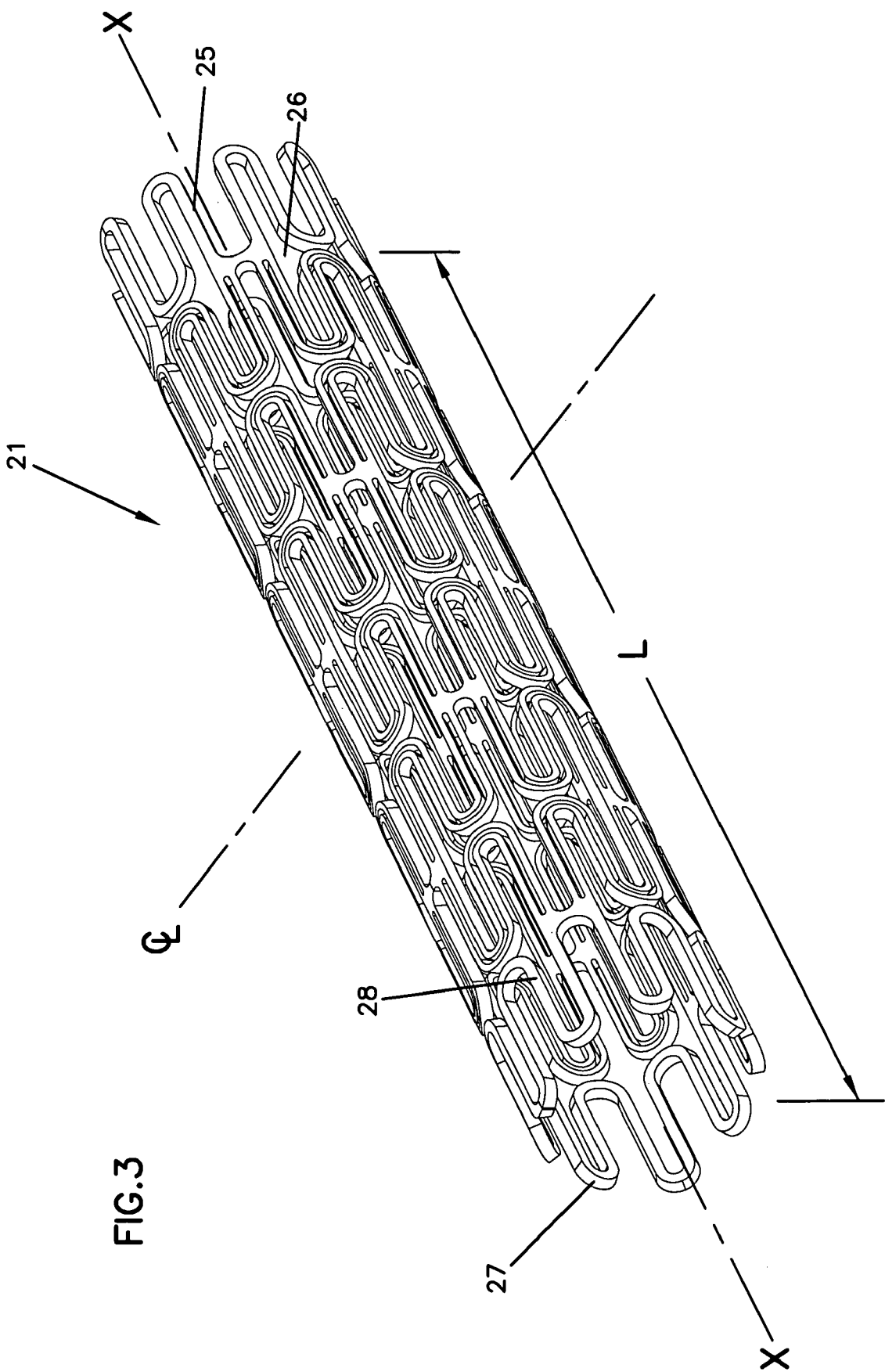
FIG. 3 is a stent of a type suitable for use in connection with the present invention.

FIG. 3 illustrates a stent 21 suitable for use in connection with the present invention. In one embodiment, the stent 21 comprises a hollow reticulated tube. The tubular body of stent 21 is defined by a number of filaments or struts 25 which surround open cells 26. The stent 21 comprises an inner surface 27 facing the interior of the stent and an outer surface 28 facing the exterior. In a preferred embodiment, a coating (now shown) covers both the inner surface 27 and the outer surface 28. In alternative embodiments, the coating may cover only the inner surface, only the outer surface, or portions of one or both of the inner and outer surfaces. The coating may aggregate at the intersection of filaments. In a preferred embodiment, the coated stent 22 (FIG. 2) is made out of a metal or metal alloy, such as titanium, tantalum, stainless steel, or nitinol. In a preferred embodiment, the coating 24 is made by mixing together an HMG-CoA reductase inhibitor, and a carrier in which both the HMG-CoA reductase inhibitor is soluble. In a particularly preferred embodiment, the carrier is a liquid oil that adheres to the inner and outer surfaces 27, 28 of the stent 22. In other embodiments, the carrier comprises a polymer dissolved in a solvent, which is then removed, e.g., by drying, to yield a solid coating composition comprising the polymer and the HMG-CoA reductase inhibitor.

As discussed, the coated stent of this invention includes a stent and a coating composition. The coating composition is preferably a blend of HMG-CoA reductase inhibitor and a liquid oil capable of adhering to the inner surface 27 and/or the outer surface 28 of the stent 22. In another embodiment, the coating composition comprises a blend of HMG-CoA reductase inhibitor and a polymer. These two ingredients are preferably blended, e.g., mixed thoroughly but not chemically reacted to any substantial degree. Preferably the HMG-CoA reductase inhibitor is "substantially unreacted." The term "substantially unreacted," when referring to the HMG-CoA reductase inhibitor, means that the inhibitor does not chemically react with the oil, the polymer or any other component of the coating or the stent, to any degree that substantially reduces its biological activity, such as inhibiting restenosis by, e.g., inhibiting the proliferation of smooth muscle cells 14. Where the coating comprises a polymer, the reductase inhibitor is physically bound to the polymer and/or to the stent, but is not chemically bound to any significant degree. In a preferred embodiment, the carrier, whether liquid or solid, polymeric or nonpolymeric, is incapable of reacting chemically with the inhibitor, i.e., is totally non-reactive (inert) with respect to the inhibitor.

The HMG-CoA reductase inhibitor should remain active even after being coupled to the carrier to form the coating composition and even after the coating composition is applied to the stent and the device is sterilized. Preferably, the reductase inhibitor remains active when the coated stent is introduced into the body of a patient, e.g., through a lumen, and is also still active when it is released from the stent. An "effective amount" of the HMG-CoA reductase inhibitor means an amount that is sufficient, when delivered to a localized area in the body lumen of a patient, to inhibit the proliferation of smooth muscle cells in a body lumen of a patient. An "effective amount" of the carrier means an amount of carrier sufficient to provide an amount of the coating composition to substantially coat the portion of the stent that is desired to be coated, preferably the entire stent. Preferably, the carrier has no functional groups that react with the HMG-CoA reductase inhibitor under the conditions of forming the blend of the HMG-CoA reductase inhibitor and the carrier. The term "biodegradable" is applied herein to any carrier, whether polymeric or nonpolymeric, and whether liquid or solid, that breaks down in the body. The term "biostable" is applied herein to any carrier, whether polymeric or nonpolymeric, and whether liquid or solid, that does not break down in the body. The term "biocompatible" describes any material that is not harmful to and does not cause an immunological response in a body, e.g., a human being.

In accordance with methods and compositions described herein, restenosis may be prevented or lessened using localized delivery of HMG-CoA reductase inhibitors from a stent placed in a body lumen. Preferably, metal stents are coated with a biocompatible coating composition comprising a carrier containing an effective amount of an HMG-CoA reductase inhibitor. The coated stent can be deployed during any conventional percutaneous transluminal angioplasty (PTA) procedure. Controlled delivery from a stent of the active HMG-CoA reductase inhibitor, using a stent such as that described herein, in an effective amount, can inhibit the regrowth of plaque and prevent restenosis. While the stents shown and described in the various embodiments are vascular stents, any type of stent suitable for deployment in a body lumen of a patient may be used with the coatings described herein.

An important aspect of this invention is the carrier used to form the coating composition. The coating composition may comprise more than one compound in a liquid carrier. The coating composition may alternatively comprise more than one solid compound in a solid carrier. The coating composition may further comprise both a liquid carrier and a solid carrier. In a still further aspect, the coating composition may also comprise more than one type of nonpolymeric or polymeric compound in the carrier, and may further comprise both a polymeric material and a nonpolymeric material in a solid or liquid carrier. In a yet further aspect of the invention, the coating composition may comprise more than one type of HMG-CoA reductase inhibitor. In coatings created by this method, the HMG-CoA reductase inhibitors are preferably physically bound to the carrier but not chemically bound thereto. Accordingly, the chemical or molecular structure of the HMG-CoA reductase inhibitor is preferably unchanged when they are mixed with the polymers to form the coating. Therefore, when the HMG-CoA reductase inhibitor is released from the coating, it remains in the desired active form.

In order to create coatings in which HMG-CoA reductase inhibitors are physically rather than chemically bound to the polymers in the coatings, HMG-CoA reductase inhibitors and carriers are chosen such that they will not have functional groups that will react with each other under the compounding conditions of to form the coating solution.

The carriers in the coating composition may be either biodegradable or biostable. Biodegradable polymers are often used in synthetic biodegradable sutures. These polymers include polyhydroxy acids. Polyhydroxy acids suitable for use in the present invention include poly-L-lactic acids, poly-DL-lactic acids, polyglycolic acids, polylactides including homopolymers and copolymers of lactide (including lactides made from all stereo isomers of lactic acids, such as D-, L-lactic acid and meso lactic acid), polylactones, polycaprolactones, polyglycolides, polypara-dioxanone, poly 1,4-dioxepan-2-one, poly 1,5-dioxepan-2-one, poly 6,6-dimethyl-1,4-dioxan-2-one, polyhydroxyvalerate, polyhydroxyburate, polytrimethylene carbonate polymers, and blends of the foregoing. Polylactones suitable for use in the present invention include polycaprolactones such as poly(e-caprolactone), polyvalerolactones such as poly(d-valerolactone), and polybutyrolactones. Other biodegradable polymers that can be used are polyanhydrides, polyphosphazenes, biodegradable polyamides such as synthetic polypeptides such as polylysine and polyaspartic acid, polyalkylene oxalates, polyorthoesters, polyphosphoesters, and polyorthocarbonates. Copolymers and blends of any of the listed polymers may be used. Polymer names that are identical except for the presence or absence of brackets represent the same polymers.

Biostable polymers that are preferred are biocompatible. Biostable polymers suitable for use in the present invention include, but are not limited to polyurethanes, silicones such as polyalkyl siloxanes such as polydimethyl siloxane and copolymers, acrylates such as polymethyl methacrylate and polybutyl methacrylate, polyesters such as poly(ethylene terephthalate), polyalkylene oxides such as polyethylene oxide or polyethylene glycol, polyalcohols such as polyvinyl alcohols and polyethylene glycols, polyolefins such as polyethylene, polypropylene, poly(ethylene-propylene) rubber and natural rubber, polyvinyl chloride, cellulose and modified cellulose derivatives such as rayon, rayon-triacetate, cellulose acetate, cellulose acetate butyrate, cellophane, cellulose nitrate, cellulose propionate, cellulose ethers such as carboxymethyl cellulose and hydroxyalkyl celluloses, fluorinated polymers such as polytetrafluoroethylene (Teflon), and biostable polyamides such as Nylon 66 and polycaprolactam. Fixed animal tissues such as glutaraldehyde fixed bovine pericardium can also be used. Polyesters and polyamides can be either biodegradable or biostable. Ester and amide bonds are susceptible to hydrolysis, which can contribute to biodegradation. However, access to water, and thus, hydrolysis, can be prevented by choosing certain neighboring chemical structures.

In a preferred embodiment, the polymer used to form the coating composition is polycaprolactone. Polycaprolactone is biocompatible, and it has a low glass transition temperature, which gives it flexibly and allows it to withstand the temperature changes stents often experience during their formation and use. For example, nitinol stents are preferably cooled to a temperature of about $-50°$ C. so that they become flexible and can be compressed and fitted onto a catheter. A sheath placed over the stent (or another restraint such as a wire binding the ends of the stent), prevents the stent from expanding as it is introduced into a patient's body at a higher temperature. The sheath or other restraint is removed at the site of the stent's use, and the stent re-expands to the size at which it is coated with a composition that includes polycaprolactone. Polycaprolactone, unlike some other stent coating materials, does not become brittle and crack throughout these fluctuations in stent temperature and size. Preferably, the polycaprolactone has a molecular weight between about 20,000 and 2,000,000, and provides a stronger and more uniform coating than lower molecular weight polymers.

Generally, the HMG-CoA reductase inhibitor is released from the stent by diffusion of the HMG-CoA reductase inhibitor out of the carrier. If the carrier comprises a biodegradable polymer, the HMG-CoA reductase inhibitor is preferably released from the stent by the degradation of the polymer. A controlled release of the HMG-CoA reductase inhibitor from the coating can be achieved with a carrier comprising both a liquid and a solid through the relatively rapid release of the diffusion of the HMG-CoA reductase inhibitor from the liquid and a slower release from the solid. In a still further embodiment, a highly controlled delivery of the HMG-CoA reductase inhibitor can be achieved by a carrier comprising a liquid, a biodegradable (preferably solid) polymer, and a biostable (preferably solid) polymer. An initial release of the HMG-CoA reductase inhibitor from the liquid may be followed by a slower release from the biodegradable solid, and a still slower release from the biostable solid.

The diffusion rate of the HMG-CoA reductase inhibitor from the carrier can be determined by release studies and the dose of the HMG-CoA reductase inhibitor can be adjusted to deliver the drug at a desired rate. In one embodiment, a higher dose of an HMG-CoA reductase inhibitor can be delivered over a short period of time by using a liquid that releases a known amount of the inhibitor within one to three days. In another embodiment, a higher dose of an HMG-CoA reductase inhibitor can be delivered over a short period of time by using a nonpolymeric liquid carrier such as vitamin E. In another embodiment, the inhibitor can be delivered via a biodegradable polymer that degrades within a few days, e.g., low molecular weight polyglycolic acid, releasing the HMG-CoA reductase inhibitor by both diffusion and/or coating degradation. In another embodiment, a biodegradable polymer which delivers an HMG-CoA reductase inhibitor primarily through diffusion is used. An example of such a polymer is polycaprolactone, which degrades after several years in the body.

Advantageously, the rate of release of a HMG-CoA reductase inhibitor from a coating can be more easily predicted and is more consistent than the rate of release of a drug from other coatings in which the drug is chemically bound to the coating. With the coatings described herein, the HMG-CoA reductase inhibitors are preferably physically released from the coatings, and thus, not dependent on a chemical step, such as hydrolysis, whose rate could vary in different patients as well as within the same patient.

The coating composition comprising the carrier and the HMG-CoA reductase inhibitor can be applied to a stent in a number of different ways. Preferably, a stent is coated in its expanded form so that a sufficient amount of coating will be applied to coat the expanded stent. In a preferred embodiment, the coating composition is at least initially applied to the stent as a liquid. Where the coating composition comprises a solid polymer, the polymer is preferably dissolved in a suitable solvent to form a polymer solution and the stent is sprayed with the solution in order to coat the stent struts. Alternatively, the polymer solution may be painted on the stent or applied by other means known in the art, such as electrodeposition, dipping, casting or molding. The solvent may then be dried to yield a solid coating composition comprising the polymer. In a preferred embodiment, the stent is dried at from 20° C. to 30° C. or ambient temperature for a period of time sufficient to remove the solvent. The drying temperature should not be high as to cause the polymer to react chemically with the HMG-CoA reductase inhibitor.

Multiple layers of the polymer solution may be applied to the stent. Preferably, each layer is allowed to dry before the next coating is applied. While an HMG-CoA reductase inhibitor is included in at least one layer of the coating, the coating solution in a second coating or other layers may optionally also contain the same or a different HMG-CoA reductase inhibitor. The polymer solution for each layer may contain the same or different polymers. The number of layers and the polymers in the layers can be chosen to deliver an HMG-CoA reductase inhibitor in a controlled manner because the rate of diffusion of the HMG-CoA reductase inhibitor through a known thickness of polymers can be estimated or measured directly.

In one embodiment, a first layer of the polymer solution, e.g., a primer layer, may be applied to improve the adhesion of the coating composition to the stent surface. Generally, coating a stent by completely encapsulating the struts of the stent is preferred. Complete encapsulation typically provides uniform distribution of a drug along the surfaces of the stent. A completely encapsulated coated stent is also more resistant than a partially coated stent to peeling and other mechanical stresses encountered during stent deployment. In certain specific embodiments, a top layer of the polymer solution without a drug may be applied on the coating. The top coating may be used to control the diffusion of the drug from the stent. The thickness of the coating is preferably 0.1 microns to 2 mm. More preferably, the thickness of the coating is from 1 to 50 microns. Most preferably, the thickness of the coating is from 10 to 30 microns. Accordingly, specific embodiments of the invention include a stent with multiple coatings or layers, e.g., films. For example, a stent with three or more coatings or layers can be provided, where the first layer (contacting the stent) comprises a first carrier material having substantially no HMG-CoA reductase inhibitor, the second layer (applied to the outer surface of the first layer) includes the HMG-CoA reductase inhibitor in a second carrier material, and the third layer (applied to the second layer) comprises a third carrier material having substantially no HMG-CoA reductase inhibitor.

In another embodiment, the polymer solution can be formed into a film and the film then applied to the stent. Any of a variety of conventional methods of forming films can be used. For example, the polymer, HMG-CoA reductase inhibitor and solvent are preferably mixed into solution and then poured onto a smooth, flat surface such that a coating film is formed after the solution is dried to remove the solvent. The film can then be cut to fit the stent on which it is to be used. The film may then be mounted, such as by wrapping, on the outer surface of a stent.

As used herein, the term "solvent" is defined according to its broadest recognized definition and includes any material into which the polymer and the HMG-CoA reductase inhibitor can dissolve, fully or partially, at room temperature or from 20° C. to 40° C. Methylene chloride is a preferred solvent. Methylene chloride's low boiling point facilitates removal from the polymer and the HMG-CoA reductase inhibitor at ambient temperatures by evaporation. However, it is contemplated that virtually any organic solvent that dissolves the polymer can be used. Solvents that can cause corrosion, such as highly acidic or basic aqueous solutions, are not preferred. Organic solvents that are biocompatible, have low boiling points and high flash points, are preferred. Other solvents that may be used include chloroform, toluene, cyclohexane, acetone, methylethyl ketone, ethyl formate, ethyl acetate, acetonitrile, n-methylpyrrolidinone, dimethyl sulfoxide, n,n-dimethylacetamide, n,n-dimethyl formamide, ethanol, methanol, acetic acid, and supercritical carbon dioxide.

In a particularly preferred embodiment, the coating composition comprises a nonpolymeric liquid that remains a liquid after it is applied to the stent and the stent is deployed within the body of a patient, i.e., the coating liquid has a melting point below body temperature (37° C.), preferably below 30° C., more preferably below room temperature (22° C.), more preferably below 20° C., still more preferably below 10° C. The liquid is preferably a viscous liquid that adheres to at least a portion of the external surface 28 of the stent 22 in sufficient quantity to deliver a therapeutically effective amount of the HMG-CoA reductase inhibitor upon expansion in the body of the patient. Although the viscous liquid may be hydrophilic, in a preferred embodiment the viscous liquid is hydrophobic. Specifically, the carrier may comprise liquid Vitamin E.

In another preferred embodiment, the viscous, hydrophobic liquid comprises a C4-C36 fatty acid or mixtures of such fatty acids, such as oleic acid or stearic acid, by way of nonlimiting example. In yet another preferred embodiment, the viscous, hydrophobic liquid comprises an oil. Exemplary oils suitable for use in the present invention include peanut oil, cottonseed oil, mineral oil, low molecular weight (C4-C36), and other viscous organic compounds that behave as oils such as, by way of nonlimiting example, 1,2 octanediol and other low molecular weight alcohols and polyols. Spraying the stent with the liquid carrier results in a coating of uniform thickness on the struts of the stent. In another embodiment, the stent may be dip coated or immersed in the solution, such that the solution completely coats the struts of the stent. Alternatively, the stent may be painted with the solution, such as with a paint brush. In each of these coating applications, the entirety of both the outer and inner surfaces of the stent are preferably coated, although only portions of either or both surfaces may be coated in some embodiments.

In yet a further embodiment of the present invention the coating composition comprises a nonpolymeric compound that is a solid at room temperature but becomes a liquid at or near body temperature. In particular, the coating composition comprises low molecular weight waxes and derivatives having a melting point at between about 30° C. and 40° C., more particularly from about 35° C. to 40° C. and more particularly about 36° C. to about 38° C. In preferred embodiments, the low melting solid is applied to the stent by heating the solid to above its melting point, then sprayed, painted, dipped, molded, or otherwise applied to the stent as a liquid and allowing the liquid to resolidify upon cooling. The stent may then be deployed in the body lumen, whereupon the coating composition re-liquifies.

In a preferred embodiment, the HMG-CoA reductase inhibitor used in the coating composition is cerivastatin. Cerivastatin is a very potent HMG-CoA reductase inhibitor. For example, when it is administered systemically, a therapeutic dose of cerivastatin is less than 1 mg per day, while other HMG-CoA reductase inhibitors must be administered in 50 mg doses. A thinner stent coating can be used if cerivastatin is the chosen HMG-CoA reductase inhibitor instead of other HMG-CoA reductase inhibitors because less coating is needed. For example, a stent coating preferably has a thickness of about 10-100 µm. If less drug and less coating to carry the drug are required, a stent coating having a preferable thickness of 10-25 µm can be used. A thinner stent coating may be preferred because it leaves more of the arterial lumen open for blood flow. Thinner coatings are also useful in preserving sidebranch access. Sidebranches are small blood vessels that branch out from the corollary artery and provide blood to some part of the heart.

Cerivastatin has other properties, in addition to its ability to inhibit the proliferation of smooth muscle cells that can contribute to restenosis, making it a desirable component of stent coatings. For example, cerivastatin has anti-thrombotic activity. Stents can often be sites of thrombus formation in the body because of the immunologically-triggered aggregation of different cell types and blood components at the site of a foreign object in the body. Thus, including cerivastatin in a stent coating may help prevent thrombus formation at the site of the stent. Cerivastatin also promotes endothelialization, or the repair of the endothelium 12 after it is damaged, such as by the delivery and expansion of the stent in an artery or other body lumen. It is contemplated that the endothelialization triggered by cerivastatin can help repair the endothelium, and thus reduce tears in the endothelium through which smooth muscle cells and other cell types can migrate into the arterial lumen and proliferate, leading to restenosis.

Other HMG-CoA reductase inhibitors may be used in these stent coatings. For example, atorvastatin, simvastatin, fluvastatin, lovastatin, and pravastatin may be used. While these compounds are known for their antihypercholesterolemic properties, it is believed that they may have other beneficial activities, such as restenosis inhibition or inhibition of cell proliferation, when they are delivered in a localized manner, such as from a stent coating.

In one embodiment, the coating compositions described herein may include more than one type of HMG-CoA reductase inhibitor. For example, a coating composition may include cerivastatin and lovastatin. In other specific embodiments, the stent coatings described herein may include one or more drugs or bioactive compounds that inhibit restenosis and are not HMG-CoA reductase inhibitors. These drugs include, but are not limited to, rapamycin, paclitaxel, actinomycin D, nicotine, and bioactive derivatives, analogues, and truncates of the foregoing. It is contemplated that combining these drugs with an HMG-CoA reductase inhibitor will provide a more effective coating composition for inhibiting restenosis than a coating composition containing only one restenosis inhibiting agent. However, the foregoing may also be used without an HMG-CoA reductase inhibitor.

EXAMPLES

The following examples are included to demonstrate different illustrative embodiments or versions of the invention. However, those skilled in the art will, in light of the present disclosure, appreciate that many changes can be made in the specific embodiments which are disclosed and still obtain a like or similar result without departing from the spirit and scope of the invention.

Coronary stents were provided by Baylor Medical School and Sulzer Intratherapeutics. Poly(lactic acid)-co-poly(glycolic acid) (PLGA) polymer was purchased from Boehringer Ingelheim. Methylene chloride was purchased from Aldrich. Poly(ethylene-co-vinyl acetate) (EVA) copolymer was purchased from Aldrich or Polymer Sciences. Sulzer Carbomedics, Inc. provides medical grade silicone rubber.

Example 1

Figure 6:
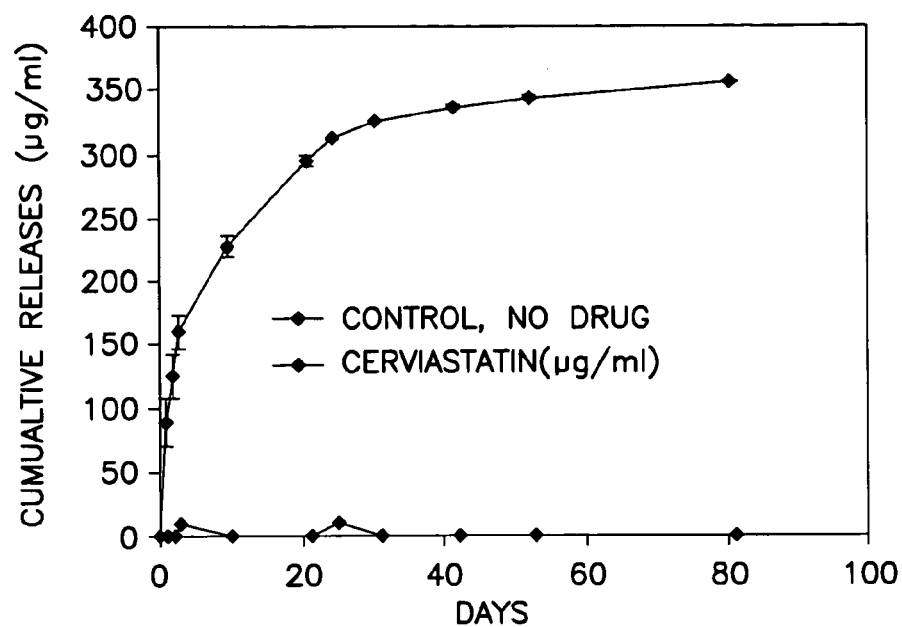
FIG. 6 is a release profile of cerivastatin released from a stent coating of polycaprolactone film.

One hundred (100) mg PCL (poly caprolactone) polymer and 10 mg of cerivastatin were dissolved in 10 ml methylene chloride solution at room temperature. The solution was poured onto a glass plate and the solvent was allowed to evaporate for 12-24 hours. After almost complete removal of the solvent, the cerivastatin-loaded PCL film was removed from the glass plate and was cut to 1.5 cm by 1.5 cm size. The film was mounted on a Palmaz-Schatz coronary endovascular stent. Control PCL films were prepared in the following manner: 100 mg PCL (poly caprolactone) polymer was dissolved in 10 ml methylene chloride solution at room temperature. The solution was poured onto a glass plate and the solvent was allowed to evaporate for 12-24 hours. After almost complete removal of the solvent, the control PCL film was removed from the glass plate and was cut to 1.5 cm by 1.5 cm size. The control film was mounted on a Palmaz-Schatz coronary endovascular stent. Release profiles were obtained for the coated stents as shown in FIG. 6.

Example 2

Figure 5:
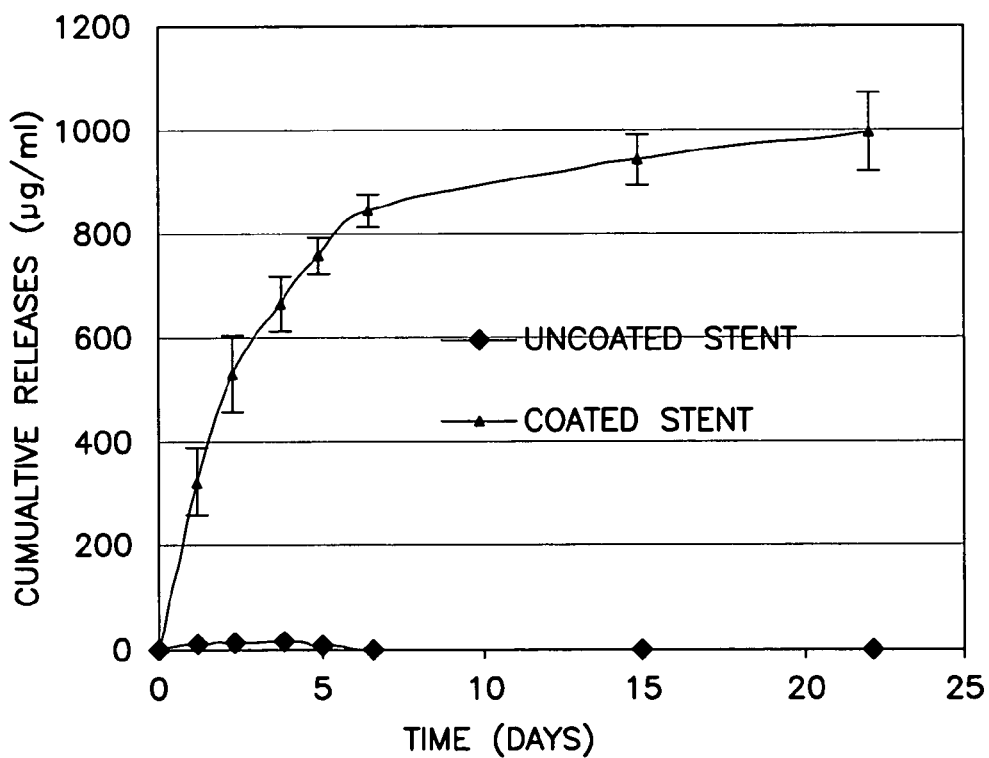
FIG. 5 is a release profile of cerivastatin released from a stent coating of EVA film.

100 mg EVA (ethylene-vinyl acetate) polymer and 10 mg of cerivastatin were dissolved in 10 ml methylene chloride solution at room temperature. The solution was poured onto a glass plate and the solvent was allowed to evaporate for 12-24 hours. After almost complete removal of the solvent, the cerivastatin-loaded EVA film was removed from the glass plate and was cut to 1.5 cm by 1.5 cm size. The film was mounted on a Palmaz-Schatz coronary endovascular stent. Control EVA films were prepared in the following manner: 100 mg EVA (ethylene-vinyl acetate) polymer was dissolved in 10 ml methylene chloride solution at room temperature. The solution was poured onto a glass plate and the solvent was allowed to evaporate for 12-24 hours. After almost complete removal of the solvent, the control EVA film was removed from the glass plate and was cut to 1.5 cm by 1.5 cm size. The control film was mounted on a Palmaz-Schatz coronary endovascular stent. Release profiles were obtained for the coated stents as shown in FIG. 5.

Example 3

A 0.6% solution of polycaprolactone dissolved in methylene chloride was prepared at room temperature. The solution was sprayed onto a Sulzer Intratherapeutics nitinol Protege model endovascular stent (6 mm×20 mm) using a semi-automated nebulizer apparatus. The nebulizer spray system provided a means of rotating and traversing the length of the stent at a controlled rate. The traversing component of the apparatus contained a glass nebulizer system that applied nebulized polycaprolactone solution to the stent at a rate of 3 ml per minute. Once applied, the 10 mg polymer coating was "reflowed" by application of 60° C. heated air for approximately 5 seconds. The process of reflowing the polymer provides better adherence to the stent surface. A drug-loaded polymer coating can be provided using this technique by first preparing a 1%-20% cerivastatin/polymer solution in methylene chloride with subsequent application to the stent surface using the same nebulizer coating system.

Example 4

Figure 7:
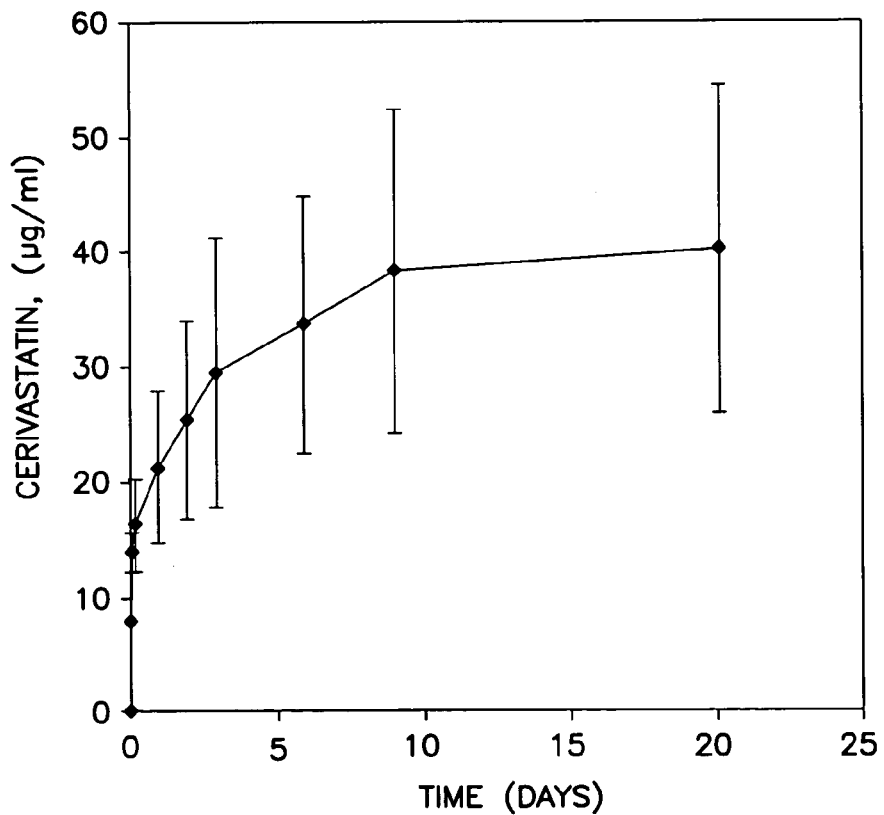
FIG. 7 is a release profile of cerivastatin released from a stent coated with silicone.

A 1% solution of uncured two-part silicone rubber dissolved in trichloroethylene was applied to a "Protege" nitinol stent in the manner described in Example 3. The coated stent was dried at room temperature for 15 minutes to allow the trichloroethylene to evaporate. Once 10 mg of silicone was coated onto the stent, the composite device containing both uncured polymer and nitinol was heated in a vacuum oven for a period of four hours in order to crosslink the silicone coating. After the coated stents were removed from the oven and allowed to cool for a period of 1 hour, cerivastatin was loaded into the silicone coating by the following method. Three mg of cerivastatin was dissolved in 300 μl of methylene chloride at room temperature. A volume of 100 μl of methylene chloride was applied to the silicone coating of each stent in dropwise fashion. In this manner, each stent was loaded with 1 mg cerivastatin, for a final concentration of 10% w/w. The crosslinked silicone absorbed the drug/solvent solution, where the solvent subsequently evaporated at room temperature, leaving behind the drug entrapped within the silicone. By this method, a diffusion-based release system for cerivastatin was created. A release profile was obtained for the coated stent as shown in FIG. 7.

Example 5

Figure 8:
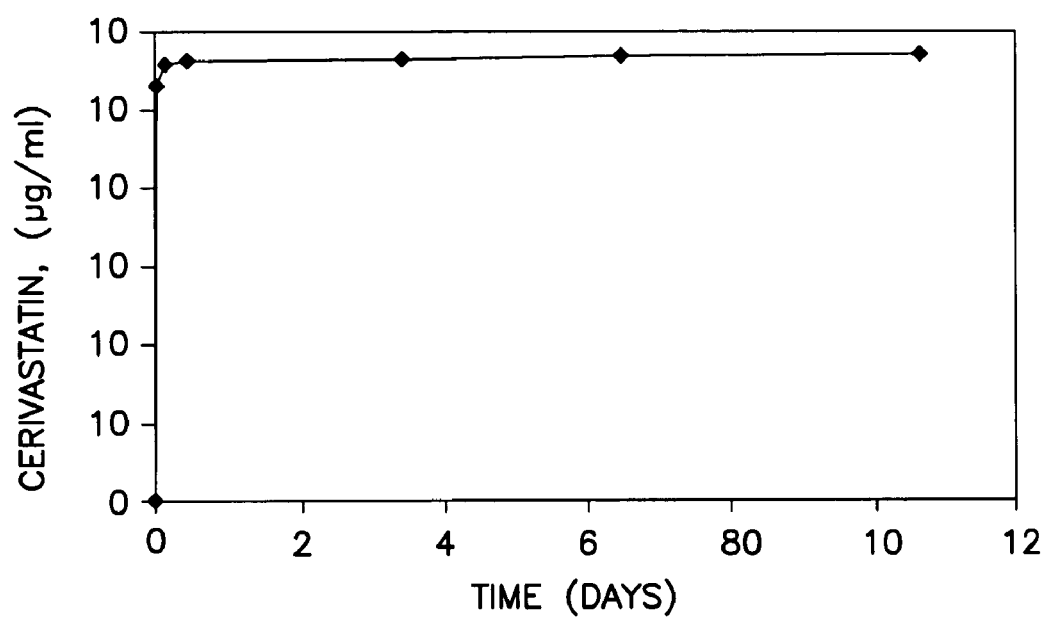
FIG. 8 is a release profile of cerivastatin released from a stent coated with liquid vitamin.

A 10% w/w solution of cerivastatin in vitamin E was created by the following method. Four mg of cerivastatin was dissolved in 100 μl of methylene chloride. This solution was added to 36 mg of liquid vitamin E and mixed manually by stirrer. The solution was allowed to stand at room temperature for 1 hour to enable the methylene chloride to evaporate from the solution. The resulting cerivastatin/vitamin E mixture was used to coat three Protege model stents by simple surface application. Approximately 10-12 mg of vitamin E and drug was deposited on each stent. A release profile was obtained for the coated stent as shown in FIG. 8.

Figure 4:
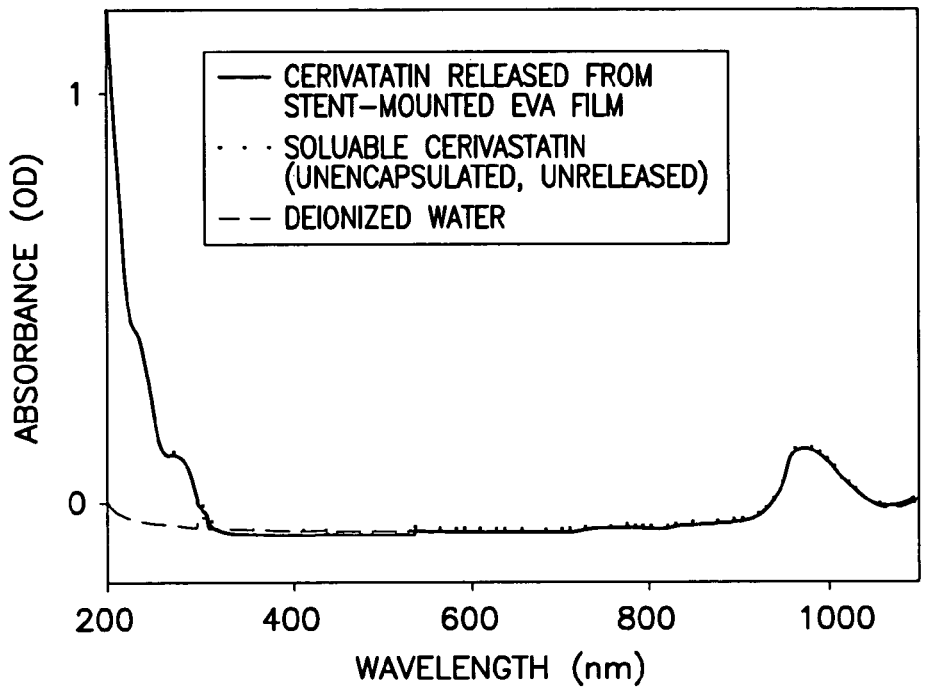
FIG. 4 is a UV-VIS spectra of cerivastatin released from a stent coating.

In preferred embodiments, the controlled release studies were done to determine the integrity and activity of cerivastatin released from stents coated with polymer and cerivastatin. Stents coated according to the process of Example 2 were immersed in an Eppendorf tube containing 1 ml phosphate buffered saline (PBS) and incubated on a rotator in a 37° C. oven. Buffer exchanges were performed at 1, 2, and 4 days following immersion in PBS. Collected samples were assayed for the spectral characteristics of cerivastatin using a UV-VIS spectrophotometer. Cerivastatin released from an EVA and cerivastatin coated stent such as the stent of Example 2 and pure cerivastatin in deionized water had almost identical UV-VIS spectra, as shown in FIG. 4, suggesting that the cerivastatin released from the stent was unaltered and thus remained biologically active.

The release of cerivastatin from stents coated according to the process of Example 2 was monitored over 7 days, as shown in FIG. 5. An EVA and cerivastatin coated stent such as the stent of Example 2 released >20 μg/ml cerivastatin per day, which is significantly higher than the 0.5 μg/ml concentration needed to inhibit proliferation of smooth muscle cells. Thus, stents produced according to this invention release a sufficient amount of cerivastatin to inhibit the proliferation of smooth muscle cells which occurs during restenosis.

The release of cerivastatin from stents coated with polycaprolactone film according to the process of Example 1 was monitored over 80 days, as shown in FIG. 6. A polycaprolactone and cerivastatin coated stent such as the stent of Example 1 released >20 μg/ml cerivastatin per day. The release of cerivastatin from stents according to the process of Example 4 was monitored over 20 days, as shown in FIG. 7. A cerivastatin and silicone coated stent such as the stent of Example 4 released >20 μg/ml cerivastatin per day.

The release of cerivastatin from stents according to the process of Example 5 was monitored over 11 days, as shown in FIG. 8. A liquid vitamin E and cerivastatin coated stent such as the stents of Example 5 released >20 μg/ml cerivastatin per day.

While the foregoing is directed to embodiments of the present invention, other and further embodiments of the invention may be devised without departing from the basic scope thereof, and the scope thereof is determined by the claims that follow, including equivalents.

The invention claimed is:

1. A coated stent comprising:
   a coating composition comprising an HMG-CoA reductase inhibitor in an effective amount, of about 1 to 50 wt.-%, and a polymeric carrier component;
   wherein the polymeric carrier component comprises a polymer selected from polycaprolactone, ethylene-vinyl acetate polymer, and a two-part silicone rubber,
   wherein the HMG-CoA reductase inhibitor is selected from the group consisting of cerivastatin, fluvastatin, simvastatin, lovastatin, atorvastatin, pravastatin and mixtures thereof, and
   wherein the HMG-CoA reductase inhibitor is released from the coated stent at a rate of >20 μg/ml per day.

2. The coated stent of claim 1, further comprising a catheter wherein the catheter and the coated stent can be coupled to form a treatment assembly.

3. The coated stent of claim 1 wherein the coating composition comprises about equal parts by weight of the HMG-CoA reductase inhibitor and the first polymeric carrier component.

4. The coated stent of claim 1 further comprises a rapamycin compound.

5. The coated stent of claim 1 which further comprises one or more bioactive compounds are selected from the group consisting of paclitaxel, actinomycin D, rapamycin, and mixtures thereof.

6. The coated stent of claim 1 which further comprises one or more bioactive compounds are selected from the group consisting of analogs of paclitaxel, actinomycin D, rapamycin, and mixtures thereof.

* * * * *